United States Patent [19]

Martin et al.

[11] Patent Number: 4,664,103

[45] Date of Patent: May 12, 1987

[54] DISPOSABLE SURGICAL DRAPE FOR CARDIOVASCULAR PROCEDURES

[75] Inventors: Jeffrey A. Martin, Duluth; Philip S. Pomeroy, Marietta, both of Ga.

[73] Assignee: Kimberly-Clark Corporation, Neenah, Wis.

[21] Appl. No.: 683,297

[22] Filed: Dec. 18, 1984

[51] Int. Cl.⁴ ............................................. A61F 13/00
[52] U.S. Cl. ................................. 128/132 D; 128/155; 128/156
[58] Field of Search ................... 128/132 D, 155, 156

[56] References Cited

U.S. PATENT DOCUMENTS

| | | | |
|---|---|---|---|
| 4,027,665 | 6/1977 | Scrivens | 128/132 D |
| 4,471,769 | 9/1984 | Lockhart | 128/132 D |
| 4,476,860 | 10/1984 | Collins et al. | 128/132 D |

*Primary Examiner*—John Kight
*Assistant Examiner*—Kriellion Morgan
*Attorney, Agent, or Firm*—William D. Herrick

[57] ABSTRACT

Disposable surgical drape especially adapted for use in cardiovascular procedures is disclosed. The drape is preferably made from a generally rectangular main sheet of a flexible, repellent nonwoven fabric. The fenestration area of the drape is substantially centrally located widthwise and extends from near the patient foot end towards the patient's chest. Preferably an additional reinforced work area is provided at the patient head directed end. The fenestration is provided by means of a split extending from the patient foot end forming tails which may be positioned as desired to shape the fenestration. The drape is positioned and the tails maintained in place by attachment to the patient with medical grade adhesive strips applied to the underside of the drape. As a particular feature of the invention, raised reinforced flaps are provided adjacent the split to provide attachment sites for clamps, tubing, cords and the like. Also, pockets are provided for containing and organizing instruments. In a preferred embodiment, the pockets are formed so that they may be opened if desired to expand the reinforced area surrounding the fenestration. Also disclosed are preferred means for assembling and folding the drape as well as preferred materials including a nonwoven laminate of spunbonded and meltblown polypropylene fibers and preferred reinforcing material of a film/foam laminate. The resulting drape contributes to the flexibility and efficiency of the operating room thereby helping to reduce surgery time and benefitting the patient.

9 Claims, 8 Drawing Figures

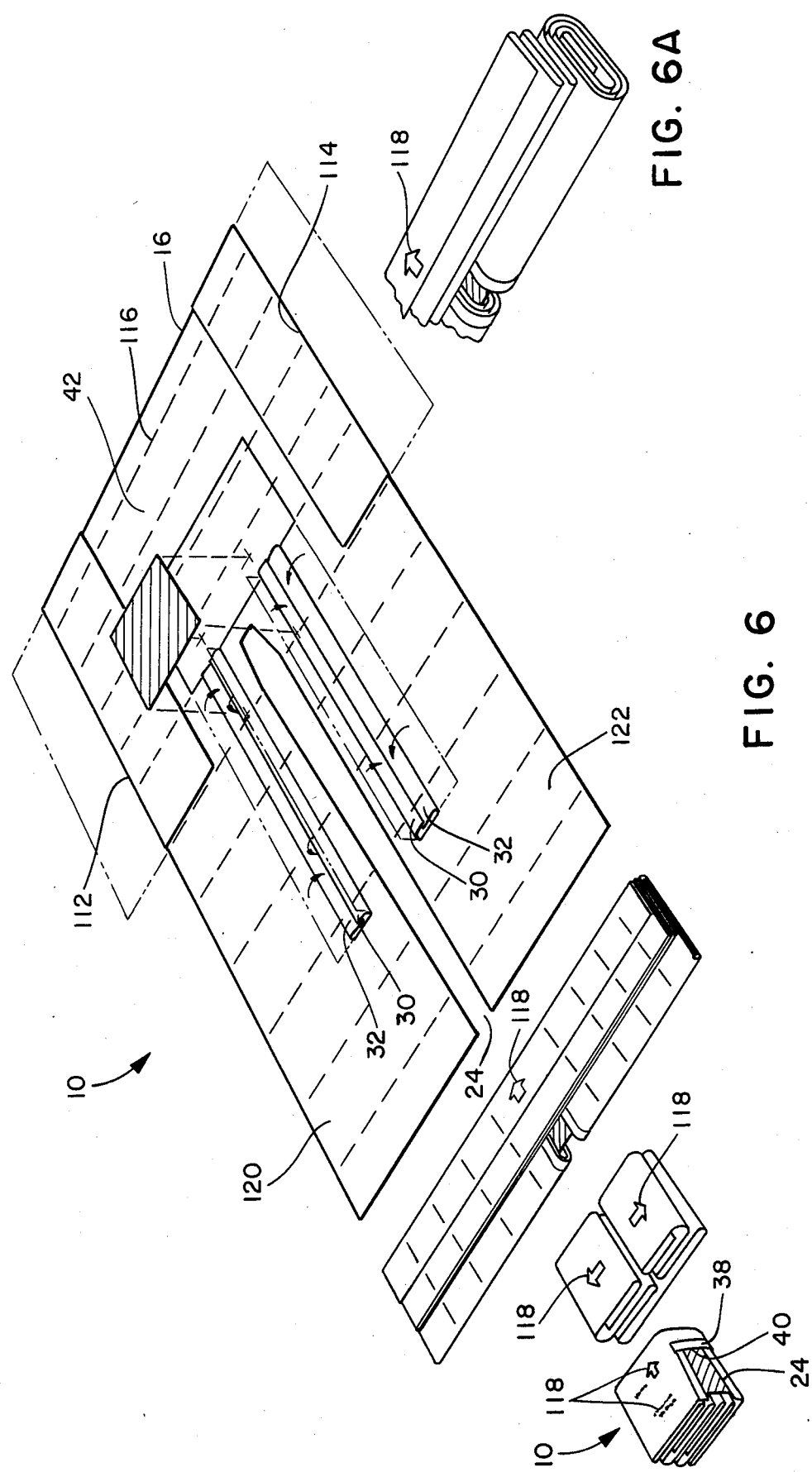

DISPOSABLE SURGICAL DRAPE FOR CARDIOVASCULAR PROCEDURES

BACKGROUND OF THE INVENTION

1. Field of the Invention

The present invention is directed to improvements in disposable drapes useful in connection with surgical procedures carried out in hospitals, clinics and the like. In particular, the present invention is directed to improvements in such drapes that are especially suited for cardiovascular surgical procedures. Such procedures are characterized by being relatively long, often several hours or more, and necessitating the use of numerous items of equipment frequently involving tubing for suctioning as well as cardioplegia lines, perfusion pump tubing and Bovie cords. Furthermore, such procedures vary in terms of the operative site as well as the size and location of incisions so that surgical drapes for use in connection therewith desirably will have wide flexibility as to the shape, size and location of the fenestration. The present invention is directed to improvements in disposable surgical drapes providing advantages in these and other features.

2. Description of the Prior Art

Disposable surgical drapes are well-known and described in numerous patents as well as literature sources. Such disposable drapes are conventionally manufactured from a wide variety of materials including cellulosic reinforced webs and nonwoven webs of various constructions. Illustrative of such disposable surgical drapes intended for general application is that described in U.S. Pat. No. 3,503,391 to Melges dated Mar. 31, 1970 which discloses a fenestrated surgical drape with reinforced operative site and adhesive attachment means and further including pocket means and a rough surface area separate from the fenestration. Modified surgical drapes intended especially for cardiovascular procedures are also described in the prior art, for example, in U.S. Pat. No. 4,027,665 to Scrivens dated June 7, 1977 and U.S. Pat. No. 4,040,418 to Collins dated Aug. 9, 1977. The former includes means for exposing both the chest and the leg areas by dual fenestrations, and the latter includes means for tying auxiliary accessories such as tubing and the like. Finally, split drapes having a fenestration slit are also well-known and described, for example, in U.S. Pat. No. 3,926,185 to Krzewenski dated Dec. 16, 1975 as well as in U.S. Pat. No. 4,479,492 to Singer dated Oct. 30, 1984.

Such prior surgical drapes, however, have not been entirely satisfactory, especially for cardiovascular and like procedures which necessitate the use or availability of widely varying equipment including those requiring the use of tubing, wires, and the like. There remains desired improvements to such drapes that would facilitate their use, particularly as regards flexibility in shaping and orienting the fenestration area and in organizing such equipment and associated tubing and wires.

SUMMARY OF THE INVENTION

The present invention is directed to improved surgical drapes particularly suited for cardiovascular procedures and including a main sheet of a flexible, repellent, nonwoven material that is generally rectangular and having one surface adapted to contact the patient and an opposing surface to be exposed during use. The drape will be of sufficient size to extend at least over the legs of the patient and has a split in the end of the drape adjacent to the area to be placed at or near the patient's feet. The split extends toward the head portion of the drape and is of sufficient dimensions at least to permit exposure of the patient's chest and one or both of the patient's legs if desired. The drape of the invention also includes pocket means adjacent to the area of the drape which may be adapted to receive tubing, cords and other equipment associated with the intended procedure. Furthermore, retaining means are included for accommodating tubing, wires and the like and maintaining them in place, and adhesive attachment means are included for positioning the drape on the patient and maintaining it in place. The adhesive is further positioned so that the fenestration area created by the split may be readily adjusted and shaped to accommodate the desired procedure. For further flexibility, the drape of the invention may be used in combination with a bar drape to permit even wider variations of fenestration size and shape. In further preferred embodiments, the drape of the invention includes reinforcement in the fenestration and pocket areas which may be a foam/film laminate and includes further means for opening at least one of the pockets to expand the reinforced area adjacent the fenestration as well as means for resisting displacement of tubing and the like once contained in the pocket. The base material for the drape of the invention may be any of a number of disposable materials that are treated for desired properties such as repellency and/or conductivity, and which may be sterilized. Examples include reinforced tissue laminates as well as nonwoven laminates of spunbonded and microfiber components. The combination of the invention provides a surgical drape particularly suited for cardiovascular procedures that greatly facilitates such procedures and enhances security, organization and accessibility of associated equipment.

BRIEF DESCRIPTION OF THE DRAWINGS

FIGS. 6 and 6A illustrate schematically a method for folding the drape of the present invention.

DESCRIPTION OF THE PREFERRED EMBODIMENTS

While the invention will be described with particular reference to cardiovascular procedures, it will be recognized by those skilled in the art that the drape of the invention may have application for other procedures as well. Cardiovascular procedures are usually time consuming, often requiring several hours or more. They also necessitate the use of many individual equipment items as well as, in many cases, suction or other apparatus having associated tubing, wires and the like. The result is that surgical drapes for cardiovascular procedures are subjected to long periods under rigorous conditions. Control and organization of tubing and wires is conventionally provided by means of clips attached through the drape material which can be a source of tears or ruptures thereby compromising the integrity of the sterile field, especially over an extended period of use. Since the purpose of the drape is to maintain a barrier surrounding the fenestration area, any rupture or tear which would disrupt this barrier is a matter of great concern.

In accordance with the present invention, a disposable surgical drape is provided that eliminates the need to clamp through the drape by providing separate clamp attachment means as well as specific means for holding tubing, wires and the like and that provides pockets for organizing and facilitating access to equipment for the surgical procedure. In preferred embodiments these pockets include a slip resistant material such as a foam-film laminate that not only reinforces but maintains the tubes, cords, instruments or the like in position. In addition, the drape of the present invention provides improved means for shaping and positioning the fenestration to further aid in the surgical procedure. The result is greater efficiency and effectiveness which may aid in speeding the draping process and in reducing the overall time required for surgery and enhance prospects for surgical patients.

Figure 1:
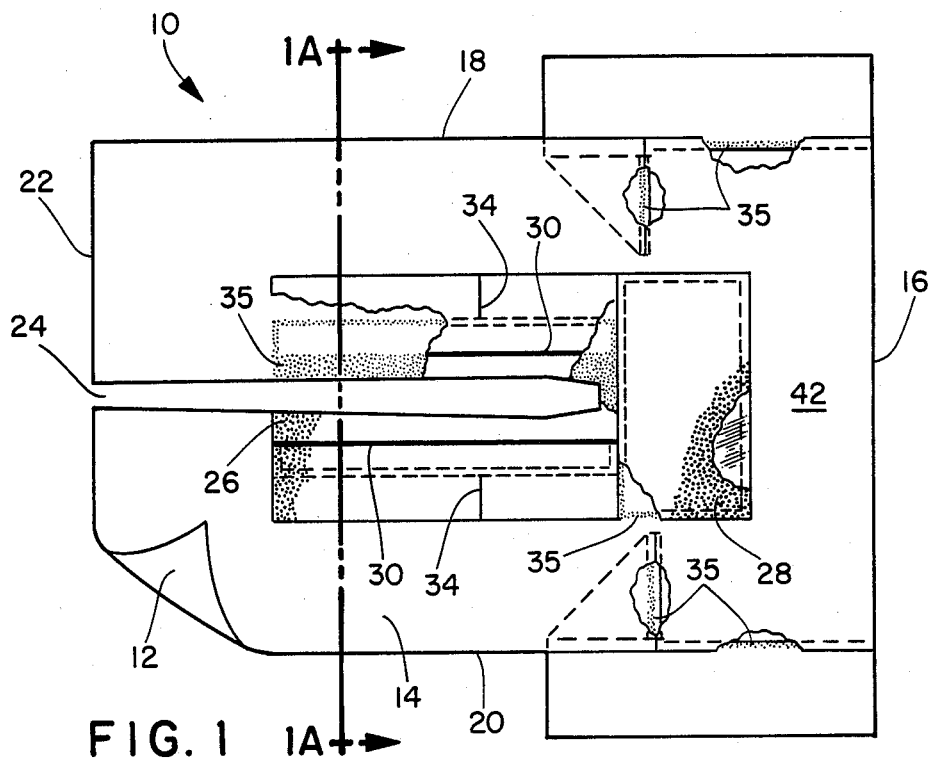
FIG. 1 is a top view of a drape in accordance with the invention.
Figure 1A:
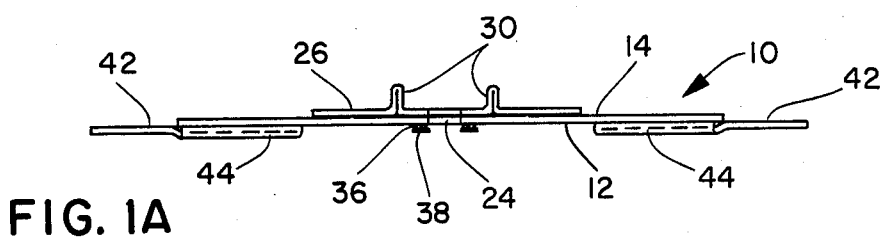
FIG. 1A is a cross-section of the drape of FIG. 1 taken along lines 1A—1A with certain details omitted for clarity.

Referring now to the drawings, wherein like numbers refer to like elements in the several views, FIG. 1 is a perspective top view of a drape in accordance with the invention. As shown, the drape 10 includes patient facing bottom surface 12 intended for contact with the patient, top surface 14 and is generally rectangular in shape having patient head edge 16, lateral edges 18, 20, and patient foot edge 22. The drape 10 further includes split 24 extending from the central area of foot edge 22 toward head edge 16 and generally parallel to sides 18 and 20 forming tail portions that may be positioned to construct a fenestration of desired configuration. On the opposite top surface 14 surrounding split 24 there is provided fenestration reinforcement 26 which is attached by means of adhesive 35 and preferably includes an exposed layer of slip resistant material such as polyurethane foam. This reinforcement area may extend past the split 24 towards head edge 16 to provide an additional reinforced area 28. Adjacent the split 24 also may be provided one or more ribs or flaps 30 of raised material suitable for securing clamps for forming pockets by folding the unattached portion of the reinforcement towards opening 24 and clamping. Pockets 32 can be used for securing tubing or the like. The dimensions of ribs 30 may vary as will be apparent to those skilled in this art so long as sufficient area is provided to attach clamps. When so clamped, the reinforcement area 26 adjacent the split 24 forms pockets 32 (FIG. 3) for receiving instruments or other equipment. Pockets 32 are preferably separated by cut lines 34 so that one or more of the pockets may be opened out to expand the area of reinforcement surrounding fenestration split 24 (FIG. 1). The cut lines are also positioned so as to permit tubing to be routed therethrough into or out of the pockets 32 at the patient chest, hip, or foot areas providing flexibility to reach equipment at different locations with reduced tubing requirements. FIG 1A shows the drape of FIG. 1 in cross-section taken along lines 1A—1A of FIG. 1. As shown, ribs 30 extend up from the plane of the drape 10 thus allowing for attachment by clamps or the like.

Figure 2:
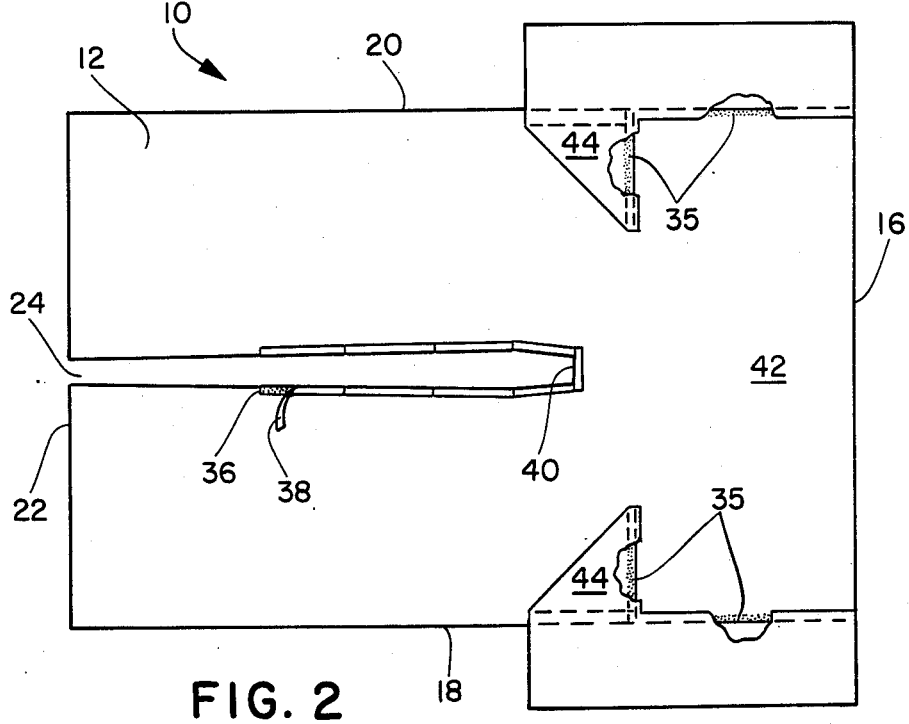
FIG. 2 is a bottom view of the drape in FIG. 1.

Turning to FIG. 2, the bottom or patient contacting surface 12 of drape 10 will be further described. As shown, split 24 is surrounded at the closed end by adhesive 36 which is covered by release strips 38. The dimensions of adhesive lines 36 may vary and may extend to the foot edge 22 if desired. In any event, the adhesive will, however, surround the closed end 40 of split 22 and extend, for example, at least about 55 inches, in many cases about 60–72 inches, toward foot end 22 of drape 10. In this Figure, it will be noted that the overall configuration of the drape is in a "T" shape and provides gusseted anesthesia screen 42 including gussets 44.

Figure 3:
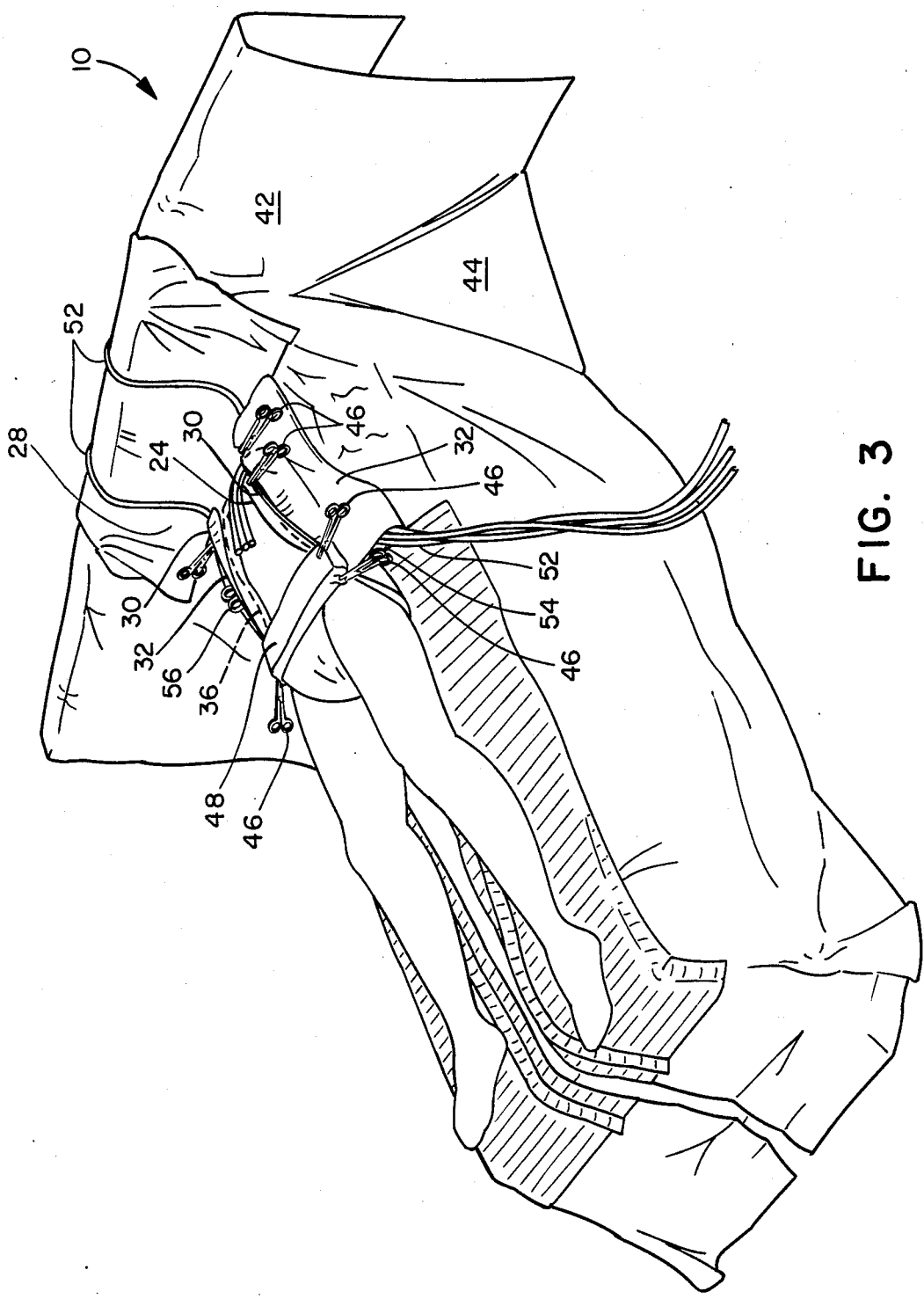
FIG. 3 is a perspective of a drape in accordance with the invention on a patient providing exposure of the patient's legs.

Turning to FIG. 3, the drape of FIG. 2 is shown in place on a patient. As shown, the drape split 24 is attached to the patient in the chest area by means of adhesive lines 36 and is draped about the torso of the patient and attached to the patient beneath the legs of the patient leaving the patient's legs exposed. Also as shown, clamps 46 are used to attach towel 48 to reinforced raised ribs or flaps 30 to stabilize positioning of drape 10 which may tend to shift due to an imbalance between weights of items in pockets 32 on opposing sides of fenestration 24 or as a result of tubing placed in or through the opening 54 formed in pockets 32. Tubes 52 are held in place by means of pocket 54, and pockets 32 contain additional instruments 56. In this embodiment panel 28 is included as part of drape 10 to provide an area where instruments may be placed. As shown, the patient thus has exposed both the chest and leg area for access in the surgical procedure, and the instruments and tubing are held securely in place by passing through the pockets formed using clamps 46 and contacting the slip resistant inner surface.

Figure 4:
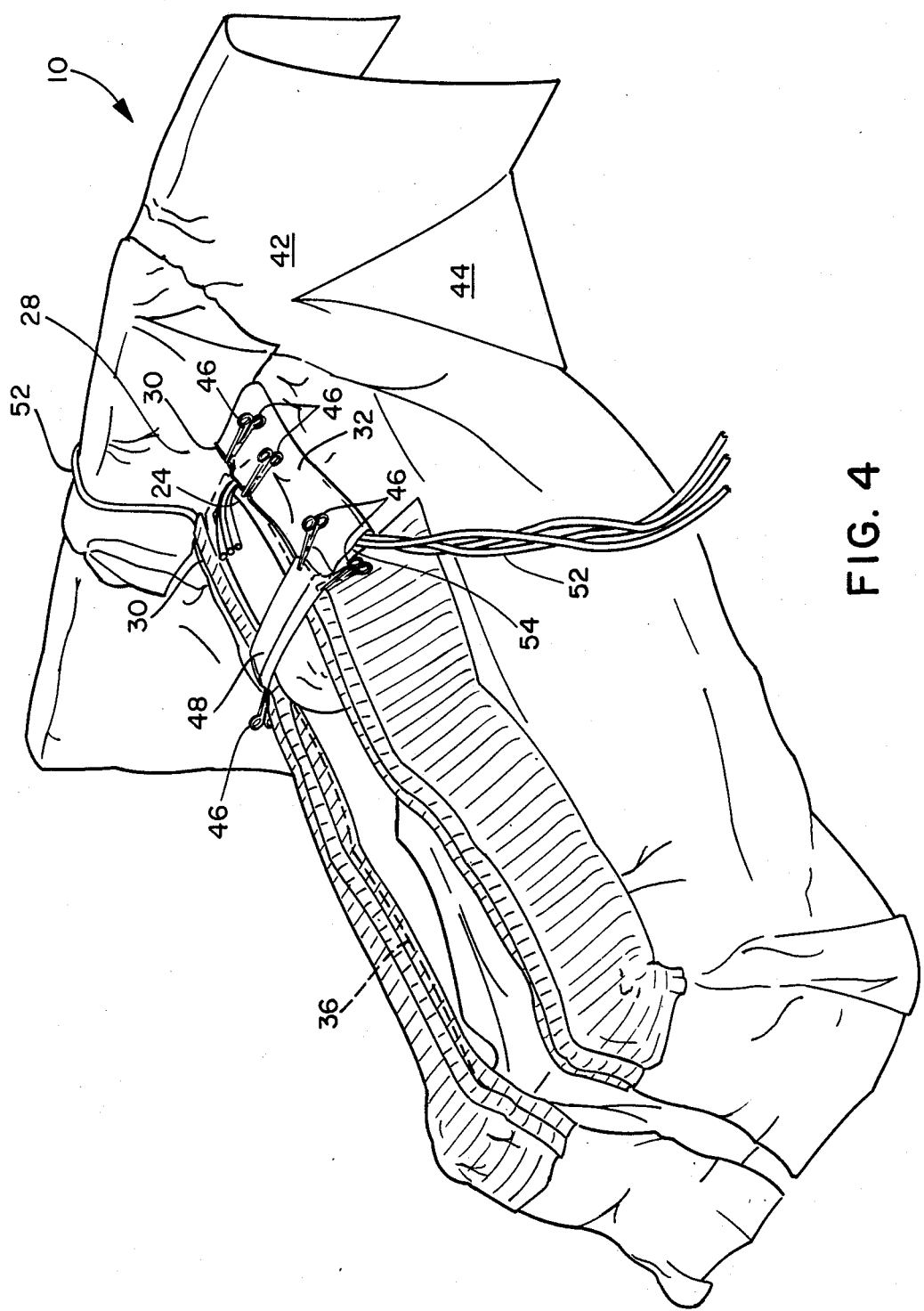
FIG. 4 is a view similar to that of FIG. 3 illustrating the drape in position covering the patient's legs.

Turning to FIG. 4, the drape of FIG. 3 is again illustrated. In this case, however, adhesive lines 36 are attached to the patient in a manner that the legs are substantially covered. If desired, an additional drape may be used to cover the legs completely. This draping procedure is particularly applicable for surgery such as valve repair, aortic surgery, or the like where access to the legs is not needed. In this case the drape of the present invention in this configuration provides ready access to the chest and groin areas while minimizing exposure of the patient's legs.

Figure 5:
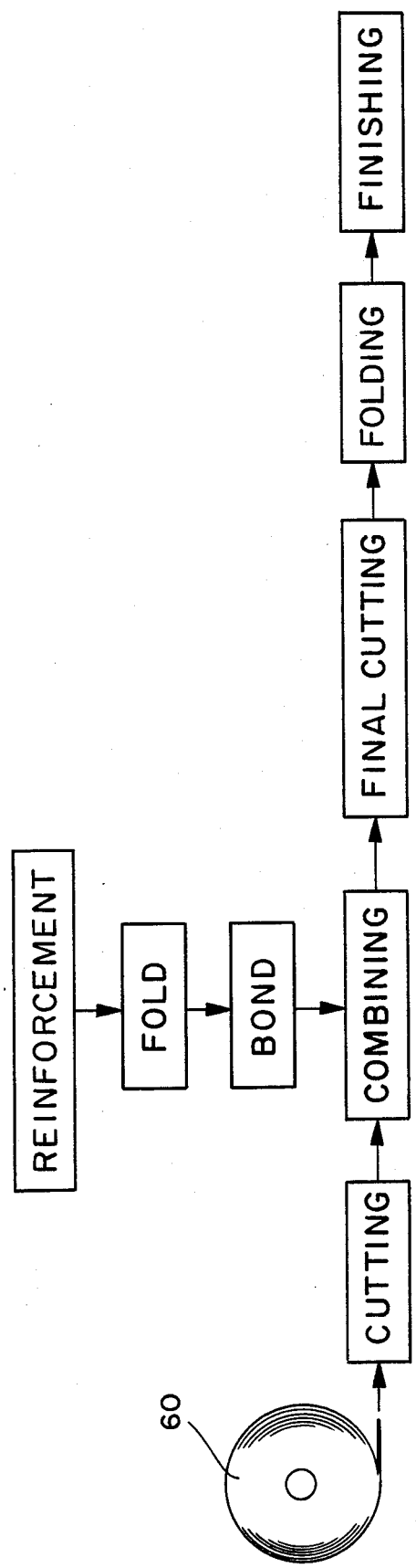
FIG. 5 illustrates schematically a method of making the drape of the present invention.

Turning to FIG. 5, there will be described means for manufacturing a drape in accordance with the present invention as illustrated in schematic form. As shown, base web 60 is directed to a cutting station where it is cut into a generally rectangular form of desired dimensions. These dimensions will depend upon the intended application but will, in general, be at least sufficient to cover the chest and leg areas of the patient. For this purpose a length of at least about 130 inches, frequently about 135 to 140 inches will be satisfactory, and a width of at least 84 inches, frequently about 85–90 inches will be satisfactory. When desired, an anesthesia screen 42 of appropriate dimensions may also be provided. The base material 60 may be any of a wide variety of nonwoven materials including water repellent reinforced cellulosic webs such as are described in U.S. Pat. No. 3,837,996 to Braun and Knauer dated Sept. 24, 1974 and available from Kimberly-Clark Corporation under the trademark KAYCEL or laminates of synthetic nonwoven fabrics such as are described in U.S. Pat. No. 4,041,203 to Brock and Meitner dated Aug. 9, 1977 may be employed. Others will be apparent to those skilled in the art.

The reinforcement panel may be separately formed by adding adhesive to the panel, folding to form tabs 30 and bonding. Conventional adhesive application means may be used such as spray, print wheels, or the like. Similar methods for achieving the folds and bonding are well-known and will be apparent to those skilled in this art. The reinforcing panel and base web are then combined and directed to a final cutting station where the fenestration cut and pocket cuts may be formed. The combination is then folded and forwarded to finishing for packaging. In general, the adhesive used may be any of the types of the medically acceptable adhesives discussed previously. The reinforcing material may be such as are in use for this purpose and will have normally a roughened or slip resistant outer surface and will be impervious to liquids. Preferably the reinforcing material is a nonslip polyurethane foam and film laminate as described, for example, in U.S. Pat. No. 3,669,106 to Shrading and Winters dated June 13, 1972. The size of the reinforcing area may also vary widely, but it will preferably be sufficient to include the intended operative site and to provide an area outside that site sufficient to support instruments or the like. For example, the reinforced area for cardiovascular drapes will preferably be generally rectangular in shape and of a length of at least about 86 inches and a width of at least 40 inches.

Turning to FIGS. 6 and 6A, a preferred method for folding the drape has been set forth. As shown, if anesthesia screen 42 is included, the ends are first folded over along lines 112 and 114 to form a rectangle. The rectangle is then folded upon itself as shown starting at the foot end to line 116 near the head end 16. The head portion is then fan folded upon itself as shown to form an elongated structure. This structure has been folded inward from both ends as illustrated in the preferred manner to present a compact package while leaving the adhesive attachment area of the closed end of the fenestration exposed for easy draping of the patient. If desired, indicia 118 may be stamped on the drape to provide instructions regarding unfolding.

In the preferred draping procedure, release strip 38 covering the adhesive surrounding of closed end 40 of split 24 is exposed and attached to the patient in the desired location. With the drape thus attached, the remaining folds may be sequentially unrolled and the additional adhesive lines sequentially attached as desired to securely retain the drape in position. In this manner draping may be done swiftly and with confidence that the placement will be accurate and secure.

As previously mentioned, the fenestration may be shaped as desired by placement of the tail portions 120 and 122 of drape 10 formed by split 24. Further flexibility in shaping the fenestration may be obtained through use of a bar sheet which comprises a rectangular sheet of drape material having adhesive along at least one of the longer sides. Through this adhesive attachment to the patient and the drape 10, the size of exposure through the fenestration may be further shaped as desired. This combination is described, for example, in U.S. Pat. No. 3,930,497 to Krebs dated Jan. 6, 1976 which is incorporated herein by reference. Alternatively, towel 48 may be used as indicated in FIG. 3 to define the fenestration area. In use, pockets 32 may be used either to retain instruments, tubing, cords or other equipment, or as illustrated in FIG. 1 may be opened to further increase the reinforced area surrounding the fenestration. In some cases it will be desirable to open one pocket only which may be accomplished by means of cut line 34. Thus the drape of the present invention provides maximum flexibility and is suitable to widely varying applications.

Thus there is apparent that it has been provided, in accordance with the invention, a surgical drape that fully satisfies the objects, aims, and advantages set forth above. While the invention has been described in conjunction with specific embodiments thereof, it is evident that many alternatives, modifications and variations will be apparent to those skilled in the art in light the foregoing description. Accordingly, it is intended to embrace all such alternatives, modifications, and variations as fall within the spirit and broad scope of the appended claims.

We claim:

1. Surgical drape comprising:
   (a) a main sheet of flexible, water repellent, nonwoven material having lateral edges, a patient head end and patient foot end, a patient facing surface and an opposite surface, said sheet having dimensions sufficient at least to cover the legs, torso, and chest areas of the intended patient;
   (b) a split in said main sheet extending from a central area of the foot end towards the head end forming tail portions and having dimensions to form a fenestration at least sufficient to permit exposure of one or both legs of the patient as desired;
   (c) pocket means disposed adjacent said split and adapted to receive equipment associated with the intended procedure wherein said pocket means includes slits permitting tubing, wires or cords to be routed through and a pocket to be opened out if desired for additional reinforcement in the fenestration area;
   (d) flaps adjacent said split for receiving means adapted to maintain tubing, wires and the like in place; and
   (e) adhesive attachment means adjacent said split on the patient facing surface and adapted to secure said drape in place on the patient while permitting adjustment of exposed patient surface area by location of said tail portions.

2. The drape of claim 1 wherein said pocket slits are located in an area intended to be adjacent to the patient's hip.

3. The drape of claim 1 or 2 further including main sheet reinforcing means adjacent said split.

4. The drape of claim 3 wherein said main sheet reinforcing means comprises a layer of nonslip polyurethane foam.

5. The drape of claim 4 wherein said pocket means also comprises a layer of nonslip polyurethane foam.

6. The drape of claim 1 wherein the main sheet is a laminate comprising layers of spunbonded polypropylene and meltblown polypropylene.

7. The drape of claim 3 including an anesthesia cage cover.

8. The drape of claim 3 wherein the patient attachment adhesive extends around the closed end of said fenestration and adjacent to the edges of said fenestration through the leg attachment portion of said tail portions.

9. The drape of claim 3 wherein said flaps comprise raised ribs of reinforcing material adjacent each side of said split.

* * * * *